United States Patent
Higashi et al.

(10) Patent No.: US 8,577,119 B2
(45) Date of Patent: Nov. 5, 2013

(54) WAFER SURFACE OBSERVING METHOD AND APPARATUS

(75) Inventors: Hiroshi Higashi, Hitachinaka (JP); Tetsuya Watanabe, Hitachinaka (JP); Kenji Aiko, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 985 days.

(21) Appl. No.: 11/698,987

(22) Filed: Jan. 29, 2007

(65) Prior Publication Data
US 2007/0269100 A1   Nov. 22, 2007

(30) Foreign Application Priority Data
Feb. 24, 2006  (JP) ................................. 2006-048136

(51) Int. Cl.
   *G06K 9/00*  (2006.01)
   *G01N 21/00*  (2006.01)
(52) U.S. Cl.
   USPC ........... 382/141; 382/145; 382/149; 382/151; 356/237.2
(58) Field of Classification Search
   USPC ................. 382/141, 152, 145, 312, 149, 151; 356/237.1, 237.2, 237.36, 394, 503, 356/401; 451/5–8, 41, 285; 438/690–693, 438/977, 401, 800, 14, 16; 355/53, 45; 430/7, 30, 321, 365; 206/454; 257/E21.56, E21.599; 216/67; 118/500; 432/253; 156/250; 211/41.18; 250/311, 492.2; 283/70, 74, 81
   See application file for complete search history.

(56) References Cited

U.S. PATENT DOCUMENTS

| | | | | |
|---|---|---|---|---|
| 5,218,426 A | * | 6/1993 | Hall et al. | 356/517 |
| 5,737,441 A | * | 4/1998 | Nishi | 382/151 |
| 5,739,899 A | * | 4/1998 | Nishi et al. | 355/53 |
| 5,811,211 A | * | 9/1998 | Tanaka et al. | 430/30 |
| 5,877,035 A | * | 3/1999 | Fujino et al. | 438/16 |
| 6,335,784 B2 | * | 1/2002 | Mishima | 355/53 |
| 6,361,646 B1 | * | 3/2002 | Bibby et al. | 156/345.1 |

(Continued)

FOREIGN PATENT DOCUMENTS

| | | |
|---|---|---|
| JP | 57-173706 | 10/1982 |
| JP | 11-281337 A | 10/1999 |

(Continued)

OTHER PUBLICATIONS

Japanese Office Action issued in Japanese Patent Application No. 2007-042241, dated Jul. 6, 2010.

(Continued)

*Primary Examiner* — Sheela Chawan
(74) *Attorney, Agent, or Firm* — McDermott Will & Emery LLP

(57) ABSTRACT

A wafer surface observing apparatus for inspecting a peripheral portion of an object has (A) a lens system and a CCD camera for taking images of the peripheral portion of the object, (B) storage for storing image data about the taken images, and (C) display for displaying the image data stored in the storage device. In particular, the present apparatus can have functions of rotating the object placed on a prealignment portion, recording images of one full outer periphery of an end portion of the object by the lens system and CCD camera into the location where the orientation flat portions or notched portions of the object are placed in position, accepting the images into the storage device, and displaying the images on a CRT.

12 Claims, 5 Drawing Sheets

(56) References Cited

U.S. PATENT DOCUMENTS

| | | | |
|---|---|---|---|
| 6,399,957 B1* | 6/2002 | Murata | 250/559.4 |
| 6,482,661 B1* | 11/2002 | Madoyski | 438/14 |
| 7,027,640 B2* | 4/2006 | Park et al. | 382/152 |
| 7,102,743 B2* | 9/2006 | Tsuji et al. | 356/237.2 |
| 7,103,505 B2* | 9/2006 | Teshima et al. | 702/183 |
| 7,138,629 B2* | 11/2006 | Noji et al. | 250/311 |
| 7,149,341 B2* | 12/2006 | Hayashi et al. | 382/145 |
| 7,161,668 B2* | 1/2007 | Meeks et al. | 356/237.2 |
| 7,180,585 B2* | 2/2007 | Kreh et al. | 356/237.2 |
| 7,220,034 B2* | 5/2007 | Li | 362/554 |
| 7,340,087 B2* | 3/2008 | Watkins et al. | 382/145 |
| 7,679,734 B2* | 3/2010 | Nonaka et al. | 356/237.2 |
| 2003/0202178 A1 | 10/2003 | Tsuji et al. | |
| 2006/0114690 A1* | 6/2006 | Iki et al. | 362/612 |
| 2008/0030644 A1* | 2/2008 | Ukawa et al. | 349/61 |
| 2009/0034829 A1 | 2/2009 | Hamada et al. | |

FOREIGN PATENT DOCUMENTS

| | | |
|---|---|---|
| JP | 2000-018919 | 1/2000 |
| JP | 2005-156537 A | 6/2005 |
| JP | 2006-064975 A | 3/2006 |
| JP | 2006-308360 A | 11/2006 |
| JP | 2007-188975 A | 7/2007 |
| JP | 2008-064595 A | 3/2008 |
| JP | 2008-196975 A | 8/2008 |
| WO | WO 03/028089 | 3/2003 |
| WO | WO 2006/112466 A1 | 10/2006 |

OTHER PUBLICATIONS

Japanese Office Action, w/ English translation thereof, issued in Japanese Patent Application No. JP 2007-042241 dated Feb. 3, 2011.

Japanese Office Action, with English translation, issued in Japanese Patent Application No. 2007-042241, dated Feb. 7, 2012.

Translation of Japanese Office Action issued in Japanese Patent Application No. 2007-042241 dated Jul. 9, 2012.

* cited by examiner

WAFER SURFACE OBSERVING METHOD AND APPARATUS

BACKGROUND OF THE INVENTION

The present invention relates to a wafer surface observing apparatus for optically inspecting foreign materials, flaws, defects, contamination, and so on (hereinafter collectively referred to as foreign matter) present on the surface of an object to be inspected and, more particularly, to a technique for observing and inspecting end portions of parts formed like flat plates such as silicon wafers, semiconductor wafers, glass substrates, or the like.

A surface observing apparatus or surface inspection apparatus for inspecting the surfaces of semiconductor wafers is shown, for example, in JP-A-2005-156537.

A wafer surface observing apparatus detects foreign matter present on the surface of a semiconductor wafer by illuminating the surface of the semiconductor wafer with an optical beam such as laser light and detecting reflected light or scattering light produced on the surface of the wafer by a photodetector.

The area on a wafer surface that can be inspected is a region excluding end portions of the wafer, irrespective of whether a pattern is formed on the surface. The end portions of the wafer indicate edges having angles produced by sawing a silicon wafer into a flat plate as well as marginal regions where a chip is not completely formed.

Since edge portions of wafer end portions have angles to the surface, reflected light or scattering light produced from the light hitting the edge portions is not incident on the photodetector. Furthermore, in marginal portions where a chip is not completely formed, film residues, delamination, and so on often occur. Reflected light or scattering light produced from the illuminating light is diffusively reflected greatly. This deteriorates the detection sensitivity of the surface observing apparatus.

Therefore, the inspected region set heretofore has excluded wafer end regions. As wafers having increased diameters are manufactured, chips are often fabricated almost up to marginal regions. It is highly likely that film residues, delamination, and so on at end portions of wafer constitute foreign matter on the surfaces of the wafers. This has greatly affected the yield.

In the past, an optical microscope has been used as a means for checking whether foreign matter on the surface of a defective wafer detected by a surface observing apparatus has been affected by roughening at ends of the wafer. With the optical microscope, observation and comparison have been made to clear up the cause (cause-effect relationship).

Therefore, an exorbitantly long time has been taken to find the cause. This has resulted in a delay in applying feedback to the process. The delay in applying feedback to the process retards yield improvement.

SUMMARY OF THE INVENTION

In coping with the foregoing problems, it is an object of the present invention to provide a function permitting one to easily observe and trace the state of end portions of a wafer in which defects are produced, over the whole process.

MEANS FOR SOLVING THE PROBLEMS

The present invention provides a wafer surface observing apparatus for inspecting peripheral portions of a wafer, the apparatus comprising: (A) a lens system and a CCD camera for imaging the peripheral portions of the wafer; (B) storage means for storing image data about obtained images; and (C) display means for displaying the image data stored in the storage device.

More specifically, the invention has functions of rotating a wafer placed on a prealignment portion, recording images about one full outer periphery of the end portions of the wafer by the lens system and CCD camera in a location where orientation flat portions or notched portions of the wafer are placed in position, accepting the images, and displaying the images on a CRT.

According to the present invention, the state of the whole wafer end portion can be observed easily. Consequently, the state of the wafer end portion that affects the yield can be easily analyzed in a related manner to the results of inspection of the surface. Feedback can be quickly applied to the process when defects are produced. Furthermore, formation of defects due to foreign matter in wafer end portions can be prevented by monitoring the states between processes.

DETAILED DESCRIPTION OF THE EMBODIMENTS

Figure 1:
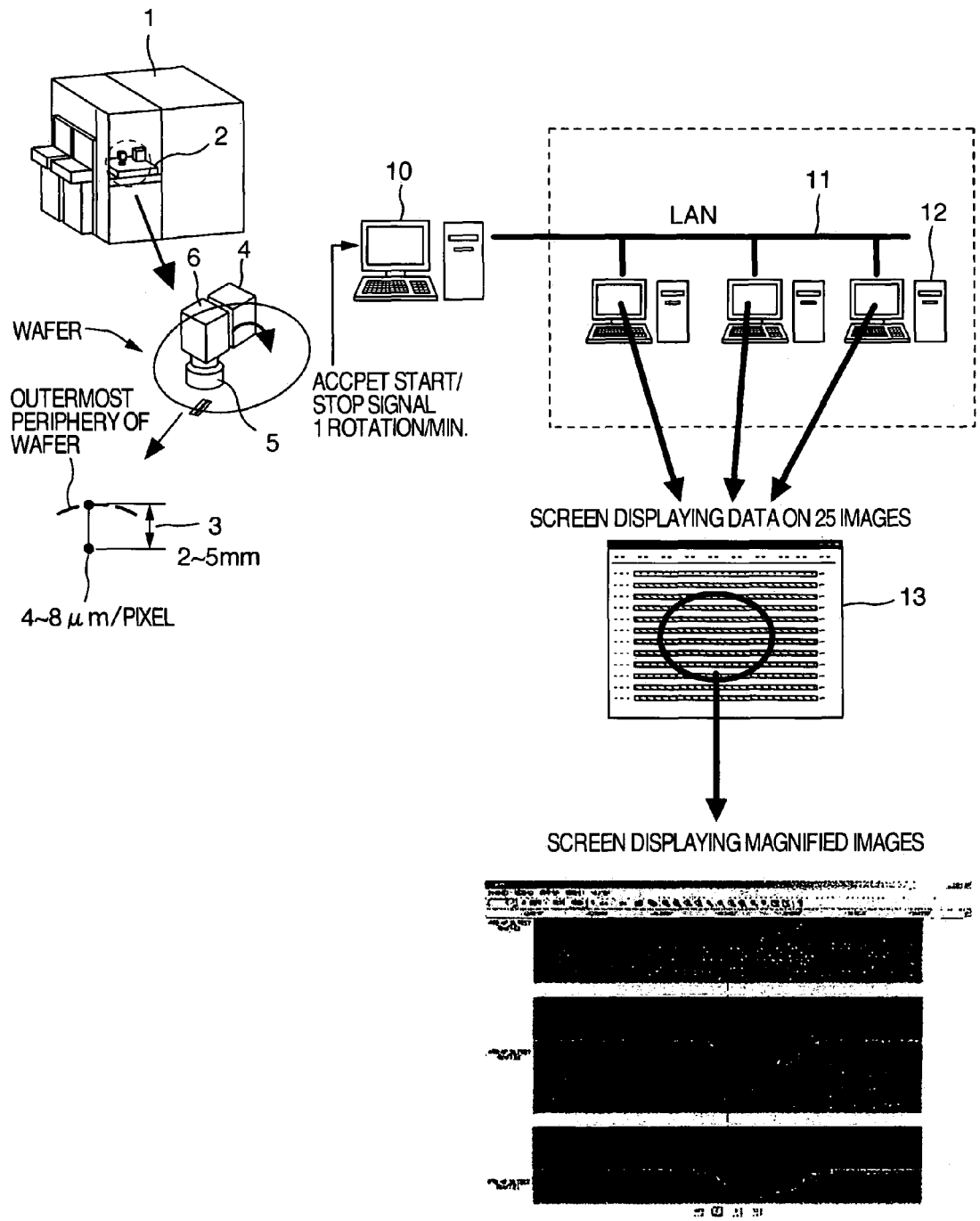
FIG. 1 is an explanatory diagram associated with Embodiment 1 of the present invention.

Embodiments of the present invention are described by referring to the drawings.

Embodiment 1

FIG. 1 is a diagram showing the structure of a surface observing apparatus of Embodiment 1 of the present invention.

Figure 2:
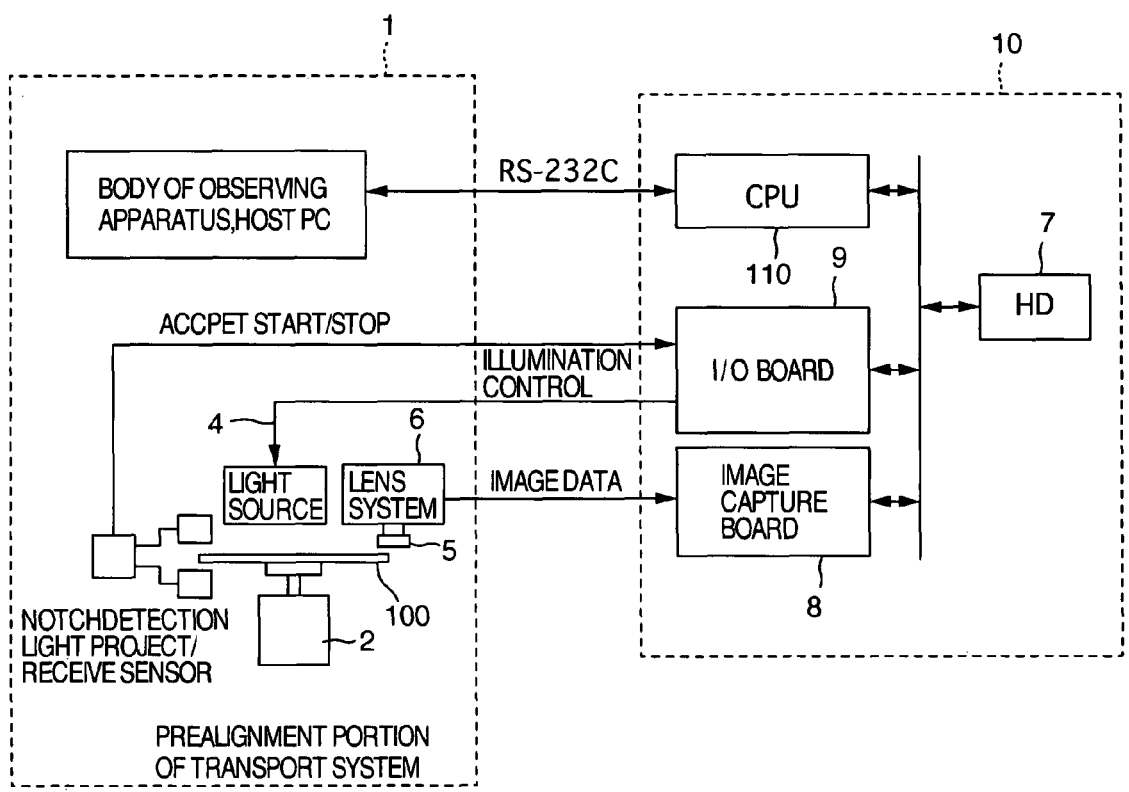
FIG. 2 is a block diagram associated with Embodiment 1 of the invention.

FIG. 2 is a block diagram showing the hardware structure of the surface observing apparatus of Embodiment 1 of the invention.

In FIGS. 1 and 2, the surface observing apparatus 1 has a prealignment portion 2 in which a light source 4 for illuminating an end portion 3 of a wafer 100, a lens system 5 for magnifying an image or images of the end portion, and a one-dimensional CCD camera 6 for converting the images into an electrical signal are installed.

The CCD camera 6 installed in the prealignment portion 2 makes it possible to record the image or images of the wafer end portion simultaneously with execution of inspection of the wafer surface. One or more of the recorded images are displayed on a display device (display means) such as a CRT.

There is a control portion 10 separate from the surface observing apparatus 1.

The control portion 10 has an image interface board 8 for accepting the electrical signal from the CCD camera 6 and sending image data (to be recorded) to a storage device 7 (storage means), an I/O interface board 9 for controlling the image acceptance timing by communications with the surface observing apparatus, and an arithmetic portion 110 for arithmetically processing image data captured by the CCD camera 6 with various programs.

Simultaneously with the inspection of the wafer surface, image data from the end portion 3 about one full outer periphery of the wafer is recorded into the storage device 7 of the control portion 10 in a related manner to the results of inspection of the wafer surface performed using wafer lot numbers, slot numbers, and so on.

The recorded image data is displayed on the display screen of the CRT (display means) of the control portion 10 or plural images can be displayed, 13, by displaying all images of the wafer end portion 3 in a lot or arbitrarily selected ones in each process step, the latter images being displayed on the display screens of CRTs (display means) of plural personal computers 12 connected via a LAN 11 from locations separate from the location where the control portion 10 is placed.

The plural displayed images can be magnified, demagnified, and scrolled right and left at will by manipulating the keyboards or mice of the personal computers 12 in such a way that the operator feels no stress. During scrolling, plural displayed images can be scrolled at the same time.

A screen showing plural images 13 shows the wafer end surfaces corresponding to overlapped lots (corresponding to 25 images). The figure located under the screen displaying plural images 13 is a screen of an enlarged display, in which three overlapped wafer end surfaces are shown. In the screen of the enlarged display, notched portions formed at end portions of the wafer are shown to be aligned.

The screen displaying plural images 13 and the screen of the enlarged display are created using program software. Image data acquired by the CCD camera 6 is data about each individual end surface image. A screen of overlapped wafer images in which the notched portions are aligned is created by arithmetic processing of a CPU 110 using the program software from the image data about each individual image.

Since many wafers can be inspected in one lot, the inspection can be done quickly. It is easy to perform comparison inspections, because the notched portions are aligned.

It is also possible to display images of offset overlapped end portions in an obliquely observed state. It is possible to cope with various inspections by preparing various kinds of program software.

Figure 3:
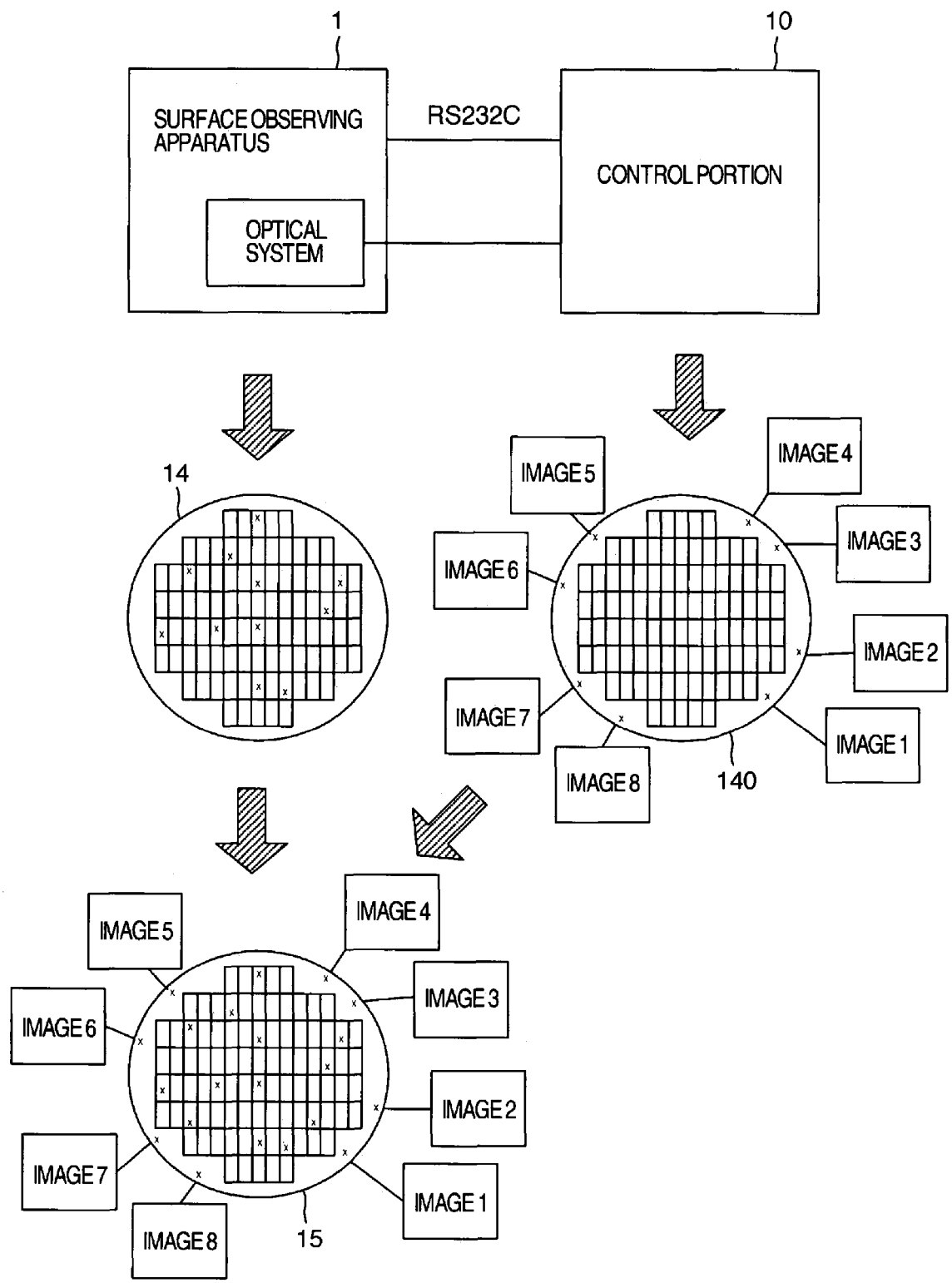
FIG. 3 is a diagram showing a map indicative of results of an inspection performed by a surface observing apparatus, the map being associated with Embodiment 1 of the invention.

FIG. 3 is a diagram showing a detected distribution of foreign matter on a wafer (hereinafter referred to as the foreign matter map 14) and images 140 recorded by the CCD camera, the foreign matter map being outputted to a CRT or printer. That is, FIG. 3 shows a combined foreign matter map 15. The combined display is also provided by the program software.

Positions on the wafer obtained by observing the images of the wafer end portions by post-inspection reviews and images are buried into the foreign matter map 14 indicating the results of a surface inspection. Thus, the state of the wafer end portions can be managed in a related manner to the results of the surface inspection.

Embodiment 2

Figure 4:
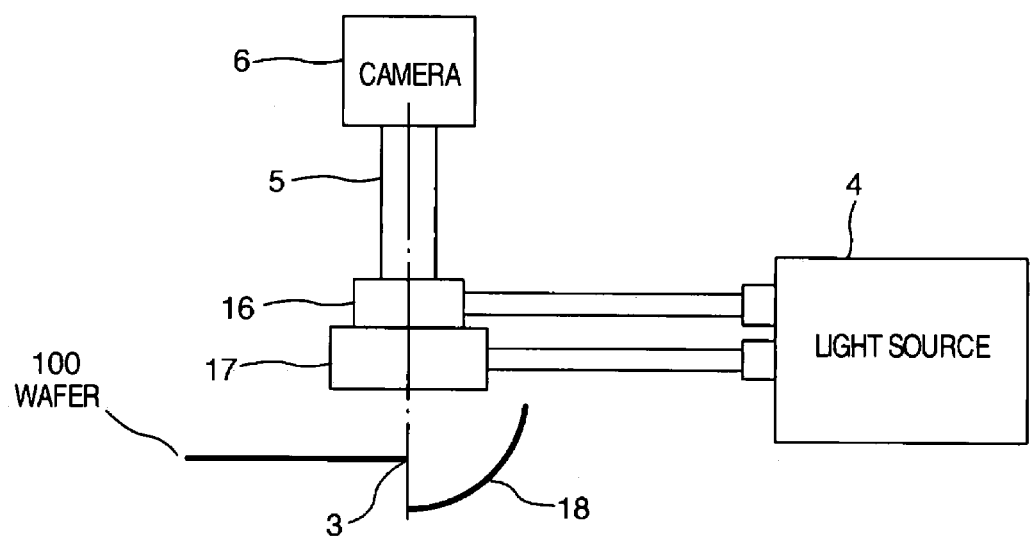
FIG. 4 is a diagram showing an illumination optical system associated with Embodiment 2 of the invention.

Embodiment 2 is described by referring to FIG. 4.

FIG. 4 is a diagram showing the structures of a lens system, a camera, and an illumination system for realizing the present invention.

The whole system is made up of an epi-illumination source 16 for illuminating peripheral portions of a wafer end portion 3, a ring illumination source 17 for illuminating the edge portion of the wafer end portion 3, a reflective plate 18 for reflecting and diffusing the illuminating light from the ring illumination source 17 to enhance the intensity of illumination on the edge portion, the lens system 5 for magnifying the images of the wafer end portion 3, and the CCD camera 6 for converting the images into an electrical signal.

Embodiment 3

Figure 5:
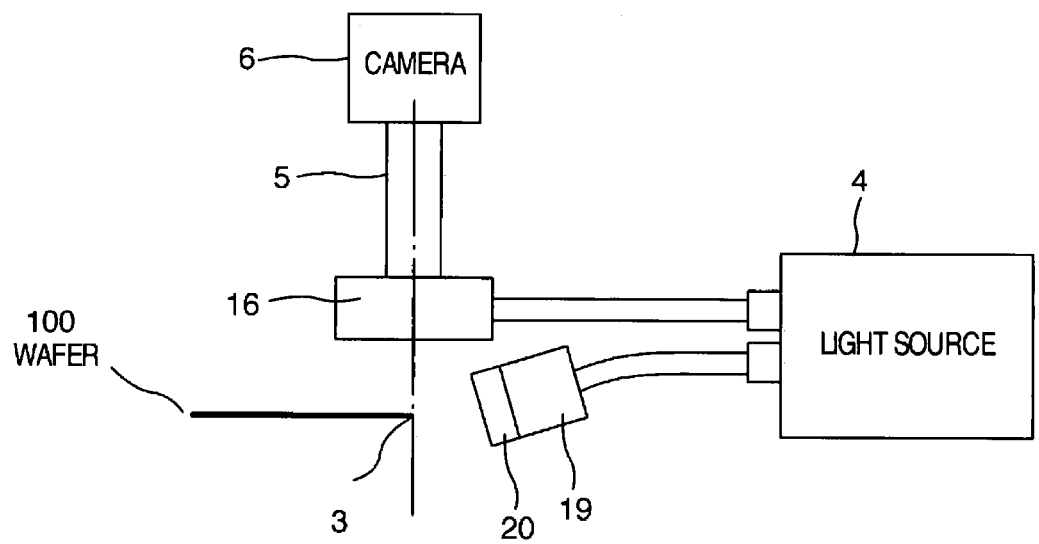
FIG. 5 is a diagram showing an illumination optical system associated with Embodiment 3 of the invention.

Embodiment 3 is described by referring to FIG. 5.

FIG. 5 is a diagram showing an example in which the illumination source for illuminating the edge portion of the aforementioned wafer end portion is composed of a line fiber 19 and a cylindrical lens 20.

Embodiment 4

Figure 6:
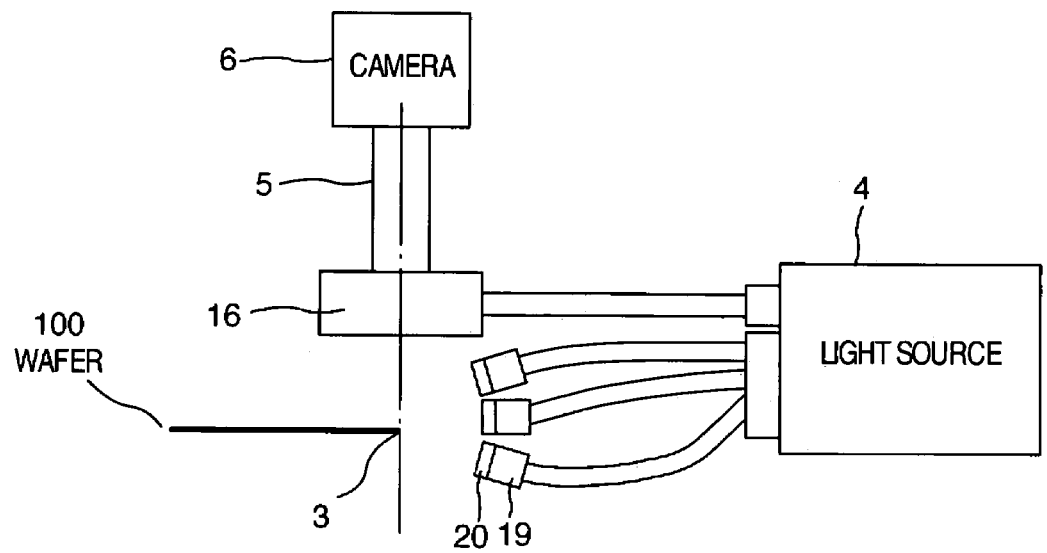
FIG. 6 is a diagram showing an illumination optical system associated with Embodiment 4 of the invention.

Embodiment 4 is described by referring to FIG. 6.

FIG. 6 is a diagram showing an example in which the above-described line fiber is split into plural parts in conformity with the curvature of the edge portion to enhance the intensity of illumination.

Embodiment 5

Figure 7:
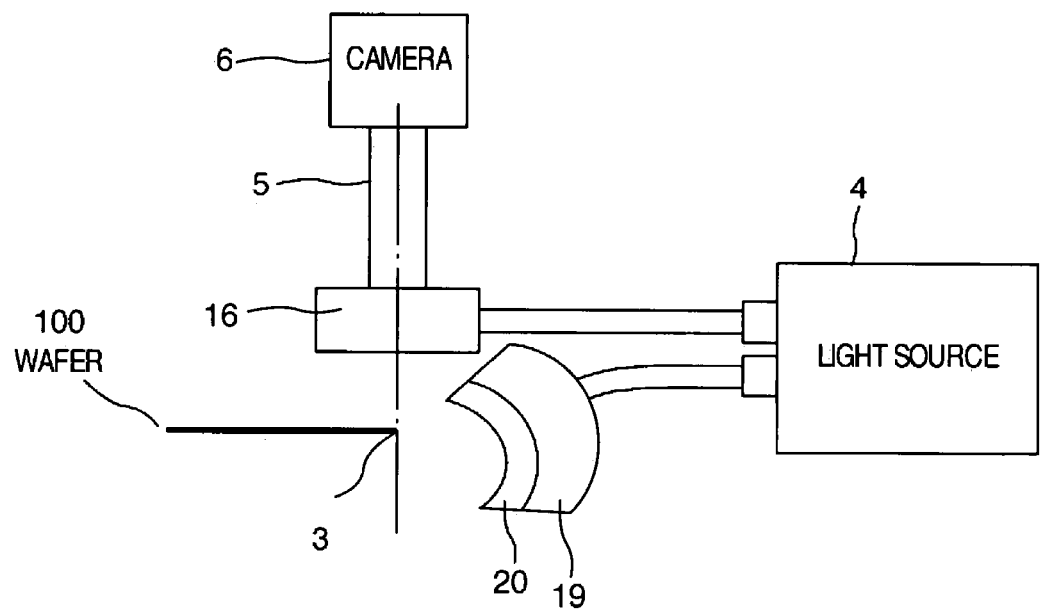
FIG. 7 is a diagram showing an illumination optical system associated with Embodiment 5 of the invention.

Embodiment 5 is described by referring to FIG. 7.

FIG. 7 is a diagram showing an example in which the above-described line fiber is shaped semicircularly in conformity with the curvature of the edge portion to enhance the intensity of illumination.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection system comprising:
   a pre-alignment unit which aligns a position of an object to be inspected;
   an edge observing unit which is arranged in the pre-alignment unit and acquires an image of an edge of the object;
   a surface inspection unit which detects a defect located inside and away from the edge of the object; and
   a processing unit which relates the image obtained with the edge observing unit to a defect map obtained with the surface inspection unit.

2. The inspection system according to claim 1, wherein the processing unit relates the image to a lot number of the object.

3. The inspection system according to claim 1, wherein the processing unit relates the image to a slot number of the object.

4. The inspection system according to claim 1, wherein the processing unit comprises an interface which controls timing for acquiring the image.

5. The inspection system according to claim 1, further comprising:
   a display unit which displays a plurality of images of the edge in a lot.

6. The inspection system according to claim 1, further comprising:
   a display unit which displays a plurality of images of the edge in process steps.

7. The inspection system according to claim 1, wherein the edge observing unit comprises:
   an illumination unit which illuminates the edge;
   a magnification unit which detects light from the edge; and
   an imaging sensor which detects light passed through the magnification unit.

8. The inspection system according to claim 7, wherein the illumination unit comprises a ring illumination unit.

9. The inspection system according to claim 8, further comprising:
   a reflection plate which reflects the light from the edge.

10. The inspection system according to claim 7, wherein the illumination unit comprises:
   a light source;
   a fiber which leads light from the light source; and
   a cylindrical lens which focuses light passed through the fiber.

11. The inspection system according to claim 1, wherein:
   the edge observing unit acquires a plurality of images at different areas of the edge, and
   the processing unit relates the defect map to the images.

12. The inspection system according to claim 1, wherein the surface inspection unit detects a defect pattern formed on the object.

* * * * *